(12) United States Patent
Trainoff et al.

(10) Patent No.: US 6,651,009 B1
(45) Date of Patent: Nov. 18, 2003

(54) METHOD FOR DETERMINING AVERAGE SOLUTION PROPERTIES OF MACROMOLECULES BY THE INJECTION METHOD

(75) Inventors: Steven P. Trainoff, Goleta, CA (US); Philip J. Wyatt, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 10/205,637

(22) Filed: Jul. 24, 2002

(51) Int. Cl.$^7$ ............................................. G01N 15/06
(52) U.S. Cl. ..................... 702/23; 702/30; 356/432; 250/574
(58) Field of Search ...................... 702/23, 22, 30, 702/31; 356/337, 338, 339, 340, 432; 250/574, 575

(56) References Cited

U.S. PATENT DOCUMENTS 5,528,366 A * 6/1996 Shortt ........................ 356/344
6,175,409 B1 * 1/2001 Nielsen et al. ............... 356/337
6,216,091 B1 * 4/2001 Hammond .................... 702/23

* cited by examiner

Primary Examiner—John Barlow
Assistant Examiner—Hien Vo
(74) Attorney, Agent, or Firm—Philip J. Wyatt

(57) ABSTRACT

A new method is presented for measuring the molecular properties of an unfractionated solution of macromolecules. Sharing some similarities with the standard Zimm plot technique, the method begins with the preparation of several sample aliquots spanning a range of concentrations. The aliquots are then injected sequentially into a stream such as provided by a liquid chromatograph. Each aliquot produces, thereby, an effective "peak" whose elements correspond to different concentrations of the diluted aliquot. By analyzing the angular and concentration dependence of the scattering signals throughout the corresponding peaks, the weight averaged molar mass, the mean square radius, and the second virial coefficient may be derived. In contrast to earlier on-line methods, better accuracy is achieved, while using a smaller quantity of sample.

9 Claims, 6 Drawing Sheets

METHOD FOR DETERMINING AVERAGE SOLUTION PROPERTIES OF MACROMOLECULES BY THE INJECTION METHOD

BACKGROUND

Molecules in solution are generally characterized by their weight averaged molar mass $M_w$, their mean square radius $$\langle r_g^2 \rangle,$$

and the second virial coefficient $A_2$. The latter is a measure of the interaction between the molecules and the solvent. For unfractionated solutions, these properties may be determined by measuring the manner by which they scatter light using the method described by Bruno Zimm in his seminal 1948 paper which appeared in the Journal of Chemical Physics, volume 16, pages 1093 through 1099. The light scattered from a small volume of the solution is measured over a range of angles and concentrations. The properties derived from the light scattering measurements are related through the formula developed by Zimm:

$$R(\theta)=K^*M_w cP(\theta)[1-2A_2 M_w cP(\theta)]+O(c^3), \qquad (1)$$

where $R(\theta)$ is the measured excess Rayleigh ratio in the direction $\theta$ per unit solid angle defined as $R(\theta)=[I_s(\theta)-I_{solv}(\theta)]r^2/I_0 V$, $I_s(\theta)$ is the intensity of light scattered by the solution a function of angle, $I_{solv}(\theta)$ is the intensity of light scattered from the solvent as a function of angle, $I_0$ is the incident intensity, $r$ is the distance from the scattering volume to the detector, $V$ is the illuminated volume seen by the detectors, $P(\theta)$ is the form factor of the scattering molecules defined as $P(\theta)=\lim_{c \to 0} R(\theta)/R(0)$, $K^*=4\pi^2(dn/dc)^2 n_0^2/(N_a \lambda_0^4)$, $N_a$ is Avogadro's number, $dn/dc$ is the refractive index increment, $n_0$ is the solvent refractive index, and $\lambda_0$ is the wavelength of the incident light in vacuum. The form factor is related to the mean square radius by $$P(\theta) = 1 - \frac{16\pi^2 n_0^2}{3\lambda_0^2}\langle r_g^2\rangle \sin^2(\theta/2) + O(\sin^4(\theta)/2) \qquad (2)$$

The collection of light scattering data over a range of scattering angles is referred to more commonly as multi-angle light scattering, MALS. The data are then fit to Eq. (1) to extract $M_w$, $$\langle r_g^2 \rangle,$$

and $A_2$. For this purpose, the reciprocal of Eq. (1) is more commonly used which may be written as:

$$K^*c/R(\theta)=1/[M_w P(\theta)]+2A_2 c+O(c^2). \qquad (3)$$

There are several methods by which the data may be fit to Eq. (3). The most popular, historically, is to mimic in software the graphical method presented by Zimm. This is often referred to as the Zimm Plot method. Alternatively one may use the global nonlinear least squares fit described below.

A powerful method of characterizing a molecular solution is to fractionate the sample first by chromatographic means, such as size exclusion chromatography, SEC, and then measure the scattered light and concentration as a function of elution volume v. If the fractionation is sufficiently resolved, each volume sample can be considered to be essentially monodisperse. If $A_2$ is known from prior experiment, or the concentrations are low enough that the effect of $A_2$ on the scattered light is negligible, one may fit the data to Eq. (1) or (3) to extract the distributions $M(v)$ and $r_g^2(v)$. This is routinely performed by commercial software such as the ASTRA® program developed by Wyatt Technology Corporation of Santa Barbara, Calif.

One may define a figure of merit, FOM, which characterizes when the $A_2$ term may be neglected. Equation (1) shows that $A_2$ is the prefactor of the $c^2$ term. By comparing the magnitude of the bracketed terms in Eq. (1), the FOM may be defined as $$\text{FOM}=2A_2 M_w c. \qquad (4)$$

When the FOM<<1, as was assumed in the derivation of the Zimm equation, the second virial coefficient has only a small effect on the light scattering signals. When one wishes to measure the second virial coefficient by light scattering, the FOM must be large enough that the effect is measurable with good precision, but it must not be made so large that higher order concentration terms are required in Eq. (1). Since SEC columns dilute the sample by about an order of magnitude per column, it is usually the case that the concentrations resulting from chromatographic separations are small enough that $A_2$ can usually be neglected. Details of the chromatographic separation methods, the definitions and calculations of the mass and size moments, and an explanation of the terminology used to describe the associated distributions may be found in the 1993 review article by Wyatt in *Analytica Chimica Acta*, volume 272, pages 1 through 40.

In summary, there are two modes of light scattering measurements. In the batch mode, a series of light scattering measurements of a single sample are made at different concentrations. The concentration and angular dependence of the scattering signals allows $M_w$, $$\langle r_g^2 \rangle,$$

and $A_2$ to be determined. In the chromatography mode, the sample composition changes as the sample elutes, so a priori knowledge of $A_2$ is required, but the distributions $M(v)$ and $r_g^2(v)$ can be measured. From the distributions, the averages $M_w$, and $$\langle r_g^2 \rangle$$

may be calculated. It should be noted that the values calculated from the fractionated sample measurements should be identical to the values measured from batch samples. Discrepancies arise from the assumption of $A_2=0$ and the distortions due to interdetector band broadening.

Although $A_2$ can be determined from batch measurements, the question remains; can the second virial coefficient be measured accurately when the sample concentration is changing continuously in time, as is the case for a chromatographic elution? In U.S. Pat. No. 5,129,723 by Howie, Jackson, and Wyatt, a method was described whereby an unfractionated sample was injected into a MALS detector following dilution and thorough mixing. This procedure produced a sample peak passing through the light scattering detector whose profile was assumed to be proportional to the concentration profile of the diluted, yet unfractionated, sample. Since the mass distribution at each slice was the same, it was assumed that each point of the profile was proportional, at that point, to the sample's concentration times the weight averaged molar mass by referring to Eq. (3) and setting $A_2=0$. On this basis, a Zimm plot could be produced using a set of these points, and the associated weight average molar mass, mean square radius, and second virial coefficient were then derived. It was thought that a concentration detector was not needed, since knowledge of the total mass injected was sufficient to convert the sample peak curve into a concentration profile. However, the method was flawed because the assumption that $A_2$ was zero contradicted the derived result that it was not.

A second method is to use a chromatography configuration, in which both a light scattering and a concentration detector are used. If one injects a monodisperse sample, or develops the chromatography method to fractionate peaks that are monomeric, the weight average molar mass at each eluting fraction should be constant throughout each peak. From the MALS and concentration data, a Zimm plot analysis may be performed from values at several different slices or sets of slices of the elution profile. The weight average molar mass, mean square radius, and second virial coefficient then may be derived. However, for most proteins, the mean square radius is too small to be accurately measured.

While this method may work in principle, there are practical difficulties that prevent it from being generally applicable. The experimental setup described above requires two detectors. Since the fluid must pass through capillaries and unions as it travels between the detectors, mixing and diffusion give rise to "interdetector band broadening". The downstream peak is "broader" than the upstream peak. This means that a monodisperse sample will produce a measured mass distribution that appears polydisperse, unless the broadening effect is taken into account. This effect is particularly problematic for proteins, since their FOMs are typically much less than one and the second virial coefficient produces a small contribution to scattered light. The error associated with band broadening usually dominates, and the derived second virial coefficient is significantly distorted. Various analytical corrections of band broadening have been developed over the years, but since the $A_2$ contribution to the light scattering signals is so small, the resulting values of $A_2$ depend sensitively on the exact model of band broadening used. This sensitive dependence on model has made this method unreliable.

Since the protein molar mass for a monodisperse sample in a suitable buffering solvent is often easily measured by MALS, mass spectroscopy, or direct sequencing, the U.S. Pat. No. 6,411,383, by Wyatt entitled "Method for measuring the second virial coefficient." emphasized the utility of circumventing the creation of the multiple concentrations required to make a full Zimm plot. However, it will be shown that when the methods described therein are extended to the more general case of multiple concentration aliquots, the method no longer requires a priori knowledge of the molar mass. Additionally the accuracy is improved due to the averaging achieved by the extended method.

Many scientists utilize on-line methods for making Zimm plots, and the afore-referenced ASTRA® program makes the determination far simpler than earlier manual methods. Currently, the best means for measuring $A_2$ of an unfractionated sample is to prepare aliquots at different concentrations and to inject them sequentially, using a syringe or syringe pump, directly into the light scattering cell of a MALS instrument. Relative to the baseline scattering of the pure solvent, each aliquot produces a ramp up to a plateau as the injection fills the cell. From a selected range of points, collectively referred to as a peak, on each of the plateaus, the software accepts the corresponding entries of the prepared concentrations and generates a Zimm plot. This approach has several shortcomings, not the least of which is the need to prepare and use relatively large amounts of sample. When injecting into a flow cell, the need to produce flat plateaus means that the cell must be overfilled several times. For a flow cell with an internal volume of 80 $\mu$l, upward of 500 $\mu$l of sample are required for each aliquot. For modem pharmaceutical research, this requirement makes the current technique infeasible. Often, this quantity of sample cannot practically be synthesized. In addition, for proteins and similar biopolymers, each injected sample must be dialyzed before injection. This adds significantly to the preparation time and labor required to make the measurement.

Lastly, in this invention, we show that by integrating across the peaks, the dependence on the peak shape is eliminated, and the band broadening correction reduces to a single parameter. The sensitive dependence on the model of broadening is removed making the method practical and reliable. Not only may $A_2$ be measured with great ease in the presence of band broadening for monodisperse samples such as proteins, but also for the case of unfractionated samples injected directly into a light scattering measurement cell.

SUMMARY OF THE INVENTION

It is a major objective of this invention to extend the methods described in the parent invention to provide a method to extract $M_w$, $$\langle r_g^2 \rangle,$$

and $A_2$ directly from a sequence of injections with different concentrations, thus eliminating the need to know $M_w$, a priori. We also disclose two fitting techniques that extract these parameters. One method is based on a global nonlinear least squares fit the data. The second analysis technique is modeled after the graphical method of Zimm. The resulting plots will be called Trainoff-Wyatt, TW, plots to differentiate them explicitly from Zimm plots. It is an objective of this invention to automate the process and eliminate, as much as possible, the manual sample preparation. Another objective of this invention is to perform the measurement more accurately by exploiting the averaging implicit in the multi-injection technique. Lastly it is an objective of this invention to make such determinations using minimal quantities of samples.

The aforementioned U.S. Pat. No. 6,411,383 by Wyatt concerns a method by which the second virial coefficient of a sample comprised of a monodisperse molar mass distribution in a solvent could be determined directly from a single injection. The same method could be applied also to certain classes of unfractionated samples. The present invention is directed to the more general application of using a series of concentration injections. The Wyatt patent requires an a priori knowledge of the sample's weight average molar mass. This invention determines $M_w$, $$\langle r_g^2 \rangle,$$

and $A_2$ using an analysis technique analogous to that presented by Zimm.

Additionally, the Wyatt patent assumes that the interdetector band broadening is negligible. It is often desirable to minimize the quantity of sample used in the measurement. Therefore small injections are used, giving rise to narrow peaks. In this case, interdetector band broadening cannot be neglected. In this invention, we present several methods to account for this effect.

The method begins with the preparation of a set of j dilutions of the sample for injection onto a SEC column set. If an auto sampler is available, then a single sample may be provided for subsequent automatic dilution to specified concentrations. There are two ways that that an autosampler may be used to prepare the dilutions. First it can inject progressively smaller quantities of the sample into the injection loop, under-filling it. Alternatively, the autosampler can pre-dilute the sample before filling the injection loop, and then fill it completely. The latter method is preferred since it will give rise to congruent concentration profiles, with different amplitudes, for each injection.

The analysis requires a set of decreasing concentrations of the sample to be measured. For the case of proteins, each sample aliquot must be dialyzed. Introducing a set of SEC columns through which each sample will flow obviates this requirement, as dialysis will occur during the passage of the sample through the column. Following the columns, a MALS detector and concentration detector are connected serially. For small molecules whose mean square radii are too small to measure, measurement at a single scattering angle such as 90° may suffice, though the precision of the determination would be diminished. These are the conventional elements of a standard separation by SEC resulting in an absolute determination of the eluting molar masses present in the sample. If neither dialysis nor fractionation is required, the separation columns can be eliminated, and the sample may be injected directly into the flow cell of the light scattering instrument. Alternatively, a guard column may be used to achieve dialysis without separation.

The intercepts of these two lines are $1/M_w$.

Figure 5:
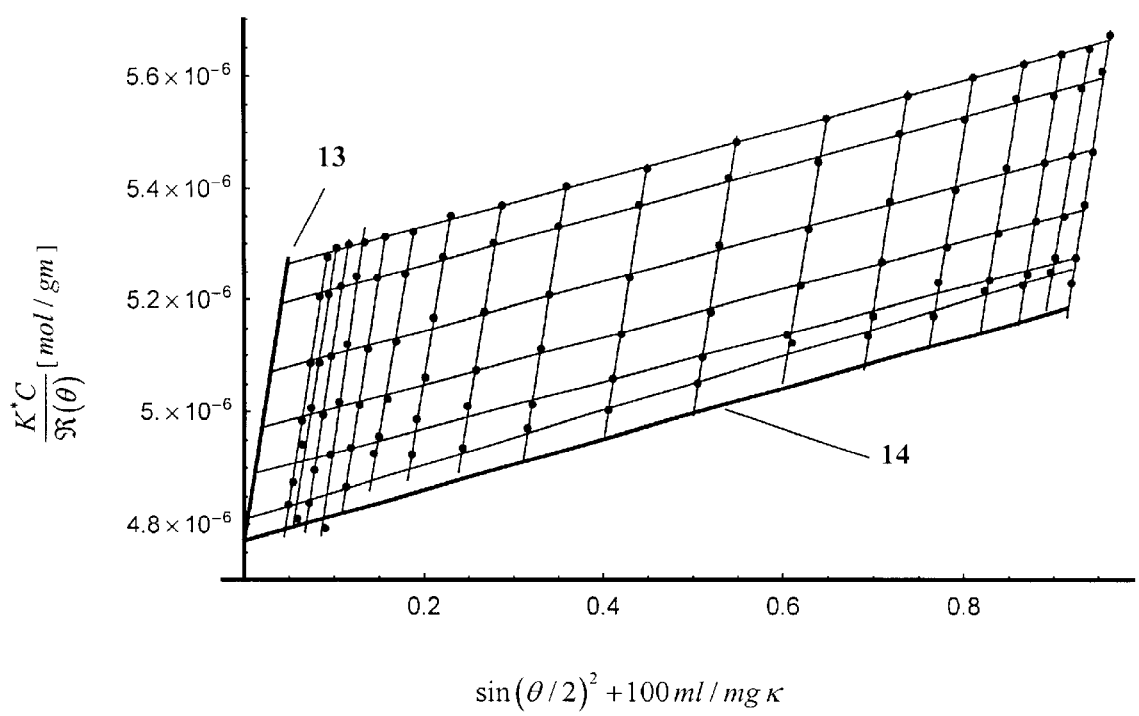
FIG. 5. Trainoff-Wyatt Plot using the Zimm fit method. The line 13 on the left of the plot is the projection of the data for each injection to zero scattering angle. The slope of this projection determines $A_2$. The line 14 at the bottom of the plot is the projection of the data for each detector to zero $\kappa$. The slope of this projection determines $$\langle r_g^2 \rangle.$$
Figure 6:
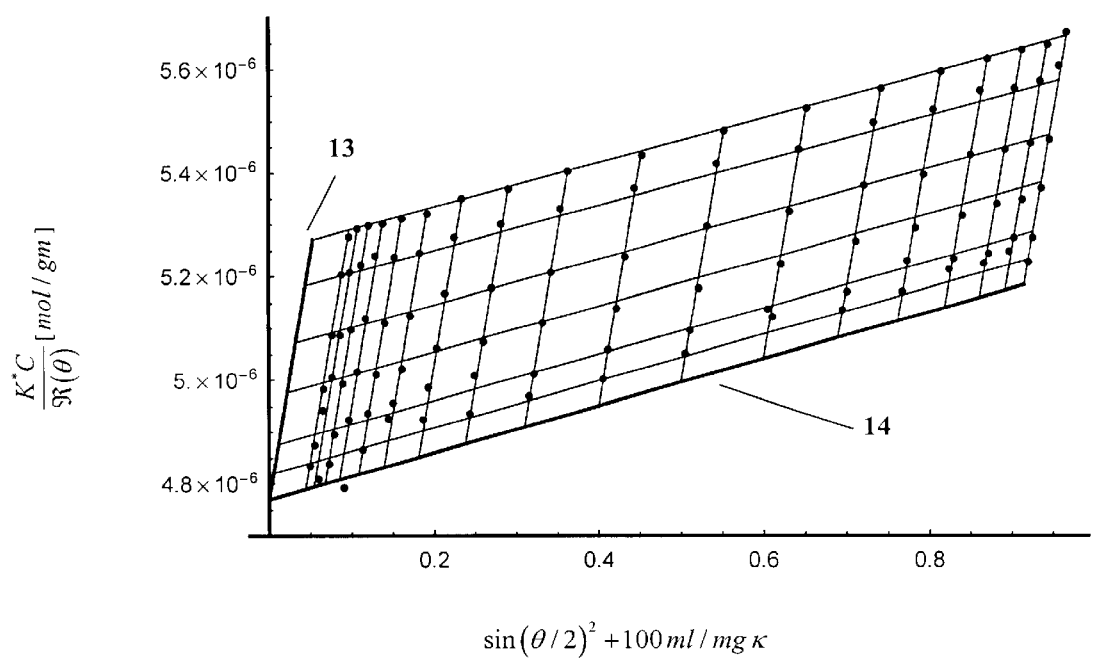

FIG. 6. Trainoff-Wyatt plot using the global fit method. The same data used in FIG. 5 was used.

DETAILED DESCRIPTION OF THE INVENTION

Theoretical Description

Let us now address the analysis method. Consider a set of injections j each corresponding to a total injected mass my. Returning to Eq. (1), for each successive peak j and scattering angle $\theta_k$, we sum the excess Rayleigh ratio and concentration peaks $$\sum_i R_{ij}(\theta_k)/K^* = M_w P(\theta_k) \sum_i c_{ij} - 2A_2 M_w^2 P^2(\theta_k) \sum_i c_{ij}^2. \quad (5)$$

Each sum is taken over all i within peak j. Note that each sum may have a different number of terms. This is because each peak may have a different width and may be spread by the effects of interdetector band broadening.

The summation on the left hand side of Eq. (5), times the factor $\Delta v$, is just the area under the excess Rayleigh ratio peak. Let us call $$R_j(\theta_k) = \sum_i R_{ij}(\theta_k),$$

which may be calculated directly. Therefore we may rewrite Eq. (5) as $$\mathfrak{R}_j(\theta_k)/K^* = M_w P(\theta_k) C_j - 2A_2 M_w^2 P^2(\theta_k) D_j, \quad (6)$$

where $$C_j = \sum_i c_{ij}$$

is proportional to the total mass eluted and $$D_j = \sum_i c_{ij}^2.$$

Since the concentration detector yields $c_{ij}$ at each elution volume, we may easily calculate the sums $D_j$ and $C_j$ of Eq. (6) over the entire broadened range of the concentration peaks. The excess Rayleigh ratios, $R_{ij}(\theta_k)$, are calculated by first subtracting the pure solvent light scattering values from the measured solution values as defined immediately following Eq. (1) above. Details are given in the earlier cited article by Wyatt in *Analytica Chimica Acda*. We now take reciprocal of Eq. (6) to obtain $$\frac{K^*}{R_j(\theta_k)} = \tag{7}$$

$$\frac{1}{M_w P(\theta_k) C_j [1 - 2A_2 M_w P(\theta_k) D_j / C_j]} \approx \frac{1 + 2A_2 M_w P(\theta_k) D_j}{M_w P(\theta_k) C_j}.$$

Thus $$\frac{K^* C_j}{R_j(\theta_k)} = \frac{1}{M_w P(\theta_k)} + 2A_2 \kappa_j + O(\kappa_j^2), \tag{8}$$

where $k_j = D_j / C_j$. We call Eq. (8) the Trainoff-Wyatt, TW, equation.

Equation (8) presents the essence of the invention. Of particular importance is the measurement and calculation of $C_j$ and $D_j$ over a range of elution slices sufficient to include all elements of the eluting sample. The number of slices included in these sums generally will be greater than the number of slices used in the calculation of the sums $\mathfrak{R}_j(\theta_k)$ due to the effects of band broadening discussed previously.

Until now, the effect of interdetector band broadening on the downstream detector has been ignored. Let us investigate the effect it has on Eq. (8). Assume that the concentration detector is downstream of the light scattering detector. Further assume that the effect of mixing and diffusion are linear so that one may write $$c^m(t) = \int_{-\infty}^{\infty} B(\tau) c(t - \tau) d\tau, \tag{9}$$

where $c^m(t)$ is the measured concentration signal, $B(\tau)$ is the normalized broadening kernel, and $c(t)$ is the concentration one would measure in the absence of interdetector broadening. We have switched notation to a continuous representation to simplify the presentation. Consider the effect that this has on C and $\kappa$ in Eq (8). If we compute C from the measured signal, we get $$C^m = \int_{-\infty}^{\infty} c^m(t) = \int_{-\infty}^{\infty} \int_{-\infty}^{\infty} dt \, d\tau \, B(\tau) c(t - \tau) \tag{10}$$

$$= \int_{-\infty}^{\infty} d\tau c(\tau) \int_{-\infty}^{\infty} dt \, B(t + \tau)$$

$$= C,$$

which follows since $B(\tau)$ is normalized. This is expected since C is proportional to the injected mass, and the broadening does not affect the injected mass. However we find that the broadening does have an effect on $\kappa$ through the measured quantity $D^m$ since $$D^m = \int_{-\infty}^{\infty} c^m(t)^2 \, dt \tag{11}$$

$$D^m = \int_{-\infty}^{\infty} dt \left( \int_{-\infty}^{\infty} B(\tau) c(t - \tau) d\tau \right)^2 \tag{12}$$

$$D^m = \int \int \int_{-\infty}^{\infty} dt \, d\tau \, d\tau' B(t - \tau) B(t - \tau') c(\tau) c(\tau') \tag{13}$$

$$D^m = \int \int_{-\infty}^{\infty} d\tau \, d\tau' c(\tau) c(\tau') \int_{-\infty}^{\infty} du \, B(u) B(u - (\tau - \tau')). \tag{14}$$

Consider the third integral on the right. This is the form of a convolution of the broadening function with itself. It is only a function of the parameter $\tau - \tau'$. We may use the convolution theorem to rewrite the third integral in Eq. (14) as $$f(\tau - \tau') = \tag{15}$$

$$\int_{-\infty}^{\infty} du \, B(u) B(u - (\tau - \tau')) = \frac{1}{2\pi} \int_{-\infty}^{\infty} d\omega \, \tilde{B}(\omega)^2 e^{-i\omega(\tau - \tau')},$$

where $\tilde{B}(\omega)$ is the Fourier transform of the broadening kernel defined by $$\tilde{B}(\omega) = \frac{1}{\sqrt{2\pi}} \int_{-\infty}^{\infty} B(x) e^{i\omega x} \, dx. \tag{16}$$

Now we further assume that the characteristic time scale of the broadening function is much smaller than that of the concentration peak. Call the two time scales $\tau_b$ and $\tau_p$ respectively. Then $\tilde{B}(\omega)^2$ is a broad peaked function with a characteristic width of $\pi/\tau_b$. Equations (15) and (14) imply that in the limit that $\tau_b \to 0$, $f(\tau - \tau') \to \delta(\tau - \tau')$, and $D^m \to D$ as expected.

The conclusion is that interdetector broadening distorts only the $\kappa$ term in the TW equation. From Eq. (14), we note that the effect of broadening is to suppress the maximum value of the peak, and to increase the values in the "wings". This means that the measured value of $D^m \leq D$. This in turn implies that the computed value of $A_2$ is overestimated. There are several approaches to correcting the data for broadening. The conceptually simplest, which turns out to be the least useful, is to deconvolve Eq. (9) to find the unbroadened concentration profile $$c(t) = \frac{1}{\sqrt{2\pi}} \int_{-\infty}^{\infty} e^{i\omega t} \frac{\tilde{c}^m(\omega)}{\tilde{B}(\omega)} d\omega, \tag{17}$$

which can then be used to compute D directly. There are several problems with this approach. One is the need to know the complete form of the broadening function. Another is that the deconvolution process is numerically unstable. Consider the ratio $\tilde{c}^m(\omega)/\tilde{B}(\omega)$ for large values of $\omega$. Since both $\tilde{c}^m(\omega)$ and $\tilde{B}(ac)$ are derived from physical measurements which include noise, and both tend towards zero for large values of $\omega$, the ratio will have large fluctuations. When the inverse Fourier Transform is performed, the result will therefore have enhanced high frequency noise. This can be filtered subsequently, but this procedure is not justifiable from first principles. What is worse is that the inverse Fourier Transform can create results that are not physically possible, such as negative values of concentration or acausal ringing. In practice, these problems make this procedure impractical. Lastly, let us note, that if these problems could be overcome, one could eliminate the process of creating a series of discrete injections, and instead use the continuous concentration variation along one injection peak as the independent parameter in a fit to Eq. (3).

For a more practical method, consider the special case in which both $c(t)$ and $B(r)$ are Gaussian. For that case, Eq. (14) can be computed explicitly from the definitions $$c(t) = \frac{c}{\tau_c \sqrt{2\pi}} e^{-t^2 / 2\tau_c^2}, \text{ and } B(\tau) = \frac{1}{\tau_b \sqrt{2\pi}} e^{-t^2 / 2\tau_b^2}, \tag{18}$$

where c is proportional to the total injected mass, and varies for each injection. Inserting Eq. (18) into Eq. (9) yields another Gaussian with width $\tau_{cm}^2 = \tau_c^2 + \tau_b^2$. We also find $$\frac{D^m}{D} = \frac{1}{\sqrt{1+\tau_b^2/\tau_c^2}} = \frac{\tau_c}{\tau_{cm}}. \quad (19)$$

However, recall that $\tau_c$ is the Gaussian width of the unbroadened peak, and in general is unknown. However, in the limit where the broadening is small ($\tau_b \ll \tau_c$), we can approximate it by the width of the light scattering peak. Therefore we can write $$\frac{D^m}{D} \approx \frac{\tau_{LS}}{\tau_{cm}}. \quad (20)$$

Both of these quantities are directly measurable. Of course, in the case where the peaks and broadening function deviate from a Gaussian profile, one would expect that Eq. (20) would begin to break down. However, it is reasonable to assume that Eq. (20) is valid when $\tau_b \ll \tau_c$, which implies that $\tau_{LS} \approx \tau_c$.

Let us return to the general problem. If one uses an autosampler to generate the dilutions, the injections will have, to a good approximation, the same shape but different amplitudes.

If one assumes that they have the same shape, we can write the jth concentration profile as $$c_j(t) = \frac{m_j}{m_0} c_0(t), \quad (21)$$

where again mi is the injected mass of the jth injection. Inserting this into Eq. (11) yields $$\frac{D_j^m}{D_j} = \frac{D_0^m}{D_0}. \quad (22)$$

We can then use Eq. (20) to approximate the ratio $D^m_0/D_0$. Alternatively, one can measure this ratio by performing the traditional plateau method of measuring $A_2$ and the TW plot, for some reference sample, and then adjusting the ratio until the two methods agree. This ratio is effectively a measurement of the interdetector broadening and should be independent of the sample used. Therefore once the system has been characterized by a reference sample, the measured ratio can be used in subsequent analysis of unknown samples.

Gathering of the Experimental Data

Figure 1:
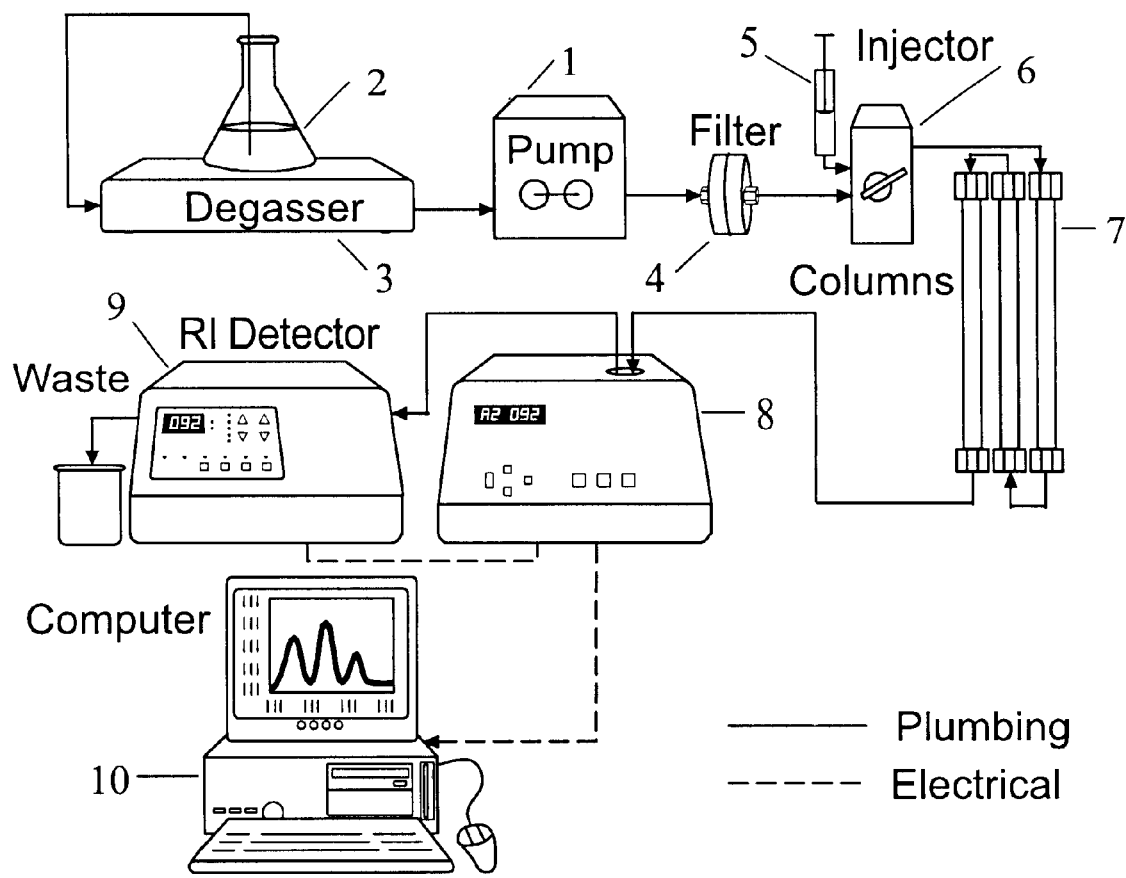
FIG. 1. Connection of the key chromatographic elements of the preferred embodiment of the invention.

In order to determine the weight average molar mass, $M_w$, mean square radius $$\langle r_g^2 \rangle,$$

and the second virial coefficient, $A_2$ of a molecular solution, a set of j samples of differing concentration are injected sequentially into a chromatographic system such as shown in FIG. 1. Solvent is drawn by pumping means 1 from a solvent reservoir 2 through a degasser 3 and then pumped through filter means 4. The degasser 3 is generally used to remove dissolved gasses from the solvent as such gasses might produce subsequently small bubbles in solution that could interfere with the desired measurements from the solution itself. Filter means 4 is generally incorporated as shown to remove residual particulate material from said solvent that could interfere with the desired measurements. Aliquots of the sample 5, whose weight average molar mass, mean square radius, and second virial coefficient are to be derived by the method of this invention, are injected by injector means 6 and pass directly through the light scattering MALS detector 8. The dilutions can be prepared in advance and injected manually. Alternatively programming an autosampler to decrease the volume of the undiluted sample, or preferentially, to dilute the sample and inject a constant volume, can create them. Typically the dilutions would span an order of magnitude, or greater. In the event the sample requires prior dialysis and/or fractionation, a selected separation column set 7 may be placed before the MALS detector 8. If there are no aggregates present, dialysis may be achieved often with the use of a guard column only, or omitted if dialysis is not required. After each successive sample 5 has passed through MALS detector 8, it flows through a concentration detector 9, shown as a differential refractive index detector, DRI, whereby the sample concentration is measured at each slice interval $\Delta v_i$. In the event that the collection intervals $\Delta v_i$ are equidistant, then $\Delta v_i = \Delta v$ is a constant. The resultant light scattering and concentration signals are then stored and processed by computer means 10 to calculate, for each injected aliquot j, the excess Rayleigh ratios, $R_{ij}(\theta_k)$, for each slice i at each measured scattering angle $\theta_k$. Computer means 10 also computes the molecular characteristics including mass and size and the distributions thereof. Although the sample concentration detector 9 is generally a DRI detector, an ultraviolet absorption detector may be substituted. An evaporative light scattering detector also may be used to monitor each eluting sample's concentration, though such a device may need special calibration, as its response is generally non-linear.

Fitting the Data to Extract the Molecular Parameters

There are two basic methods of fitting the light scattering and concentration data in order to extract $M_w$, $$\langle r_g^2 \rangle,$$

and $A_2$ from Eq. (8). The first method is based on the graphical method of Zimm, and the close resemblance of the function forms of Eqs. (3) and (8). It consists of fitting subsets of the data, in order to extrapolate to zero scattering angle and zero concentration. First the data for each angle is fit as a function of $\kappa_j$ to $$\frac{K^* C_j}{R_j(\theta_k)} = \sum_{l=0}^{N_l} a_{l,k} \kappa_j^l, \quad (23)$$

where $a_{l,k}$ are fit parameters and $N_l$ is the order of the concentration fit. If $N_l=1$, a linear fit is performed, if $N_l=2$, a quadratic fit is performed, etc. Note that $a_{0,k}$ is the extrapolation to zero concentration of the kth detector angle. Next the data for each injection is fit to $$\frac{K^* C_j}{R_j(\theta_k)} = \sum_{m=0}^{N_m} b_{j,m} \sin^{2m}(\theta_k/2), \quad (24)$$

where $b_{j,m}$ are fit parameters and $N_m$ is the order of the angle fit. Note that $b_{j,0}$ is the extrapolation of the data to zero scattering angle. Lastly, following Zimm, the fit coefficients are then fit to $$a_{0,k} = \sum_{m=0}^{N_m} u_m \sin^{2m}(\theta_k/2), \quad (25)$$

$$b_{j,0} = \sum_{l=0}^{N_l} v_l \kappa_j^l, \quad (26)$$

where $u_m$ and $v_l$ are fit coefficients. They are related to the molecular characteristics by $$M_w = 1/u_0, \, M_w = 1/v_0, \quad (27)$$

$$A_2 = v_1/2, \quad (28)$$

$$\langle r_g^2 \rangle = \frac{3\lambda_0^2 M_w u_l}{16\pi^2 n_0^2}. \quad (29)$$

It should be evident that the fitting of the measured data to the form of Eqs. (24), (25), and (26) may be done in a statistical sense whereby the data used to perform these fits may be weighted by their measured standard deviations. These are standard techniques and need no further discussion.

Equation (27) implies that $M_w$ can be computed from both the angular fits, and the concentration fits. The two methods should agree, however in the presence of experimental noise, they often differ slightly. This can be used as a consistency check to determine of the accuracy of the method. An average quantity can be defined as $$\overline{M}_w = \frac{1}{2u_0} + \frac{1}{2v_0}. \quad (30)$$

Furthermore the fits described in Equations (25) and (26) can be well visualized by a plot similar to the one presented by Zimm. These are referred to as Trainoff-Wyatt plots to differentiate them explicitly from Zimm Plots. To generate a TW plot, graph the data and the fits in Eqs. (25) and (26) by plotting $\sin^2(\theta_k/2) + k\kappa_j$ on the abscissa and $K^*C_j\Re_j(\theta_k)$ on the ordinate as shown in FIG. 5. The value k is called the "stretch factor" and is chosen so that the data from different injections do not overlap. It only affects the scale of the plot, and not the parameters determined by the fits.

The second method is to perform a global fit to the entire data set. This is in contrast to the Zimm method of performing a series of fits to subsets of the data. Zimm's method was developed in the 1940's and without the use of numerical fitting software. The global method is to define a fit function that models the data, and to perform a nonlinear least squares fit of the data to the fit function, using a standard algorithm, such as the Marquart method. The fit model is $$\frac{K^*C_j}{R_j(\theta_k)} = \sum_{l=0}^{N_l} \sum_{m=0}^{N_m} a_{lm} \sin^{2l}(\theta_k/2)\kappa_j^m, \quad (31)$$

where $a_{lm}$ are the fit parameters, and $N_l$ and $N_m$ are the fit orders of the angle and $\kappa$ fits, respectively. The fit parameters are related to the physical quantities by $$M_w = 1/a_{00}, \quad (32)$$

$$A_2 = a_{01}/2, \quad (33)$$

$$\langle r_g^2 \rangle = \frac{3\lambda_0^2}{16\pi^2 n_0^2} \frac{a_{10}}{a_{00}}. \quad (34)$$

A TW plot may also be generated from the results of the global fitting method. The only difference is that in this case, the fit from Eq. (31) is used. Also note that, unlike the previous fitting method, the molar mass is computed unambiguously in Eq. (32).

An Example of the Method

To demonstrate the utility of the method, we present the measurement of the molecular parameters of a polystyrene standard dissolved in toluene. The sample, from Pressure Chemical Corporation, has a molecular weight approximately 200 kD and is known to have a linear random coil conformation. Furthermore, the sample is very nearly monodisperse. It has a polydispersity of less than 1.01, indicating the absence of substantial quantities of aggregates.

Figure 2:
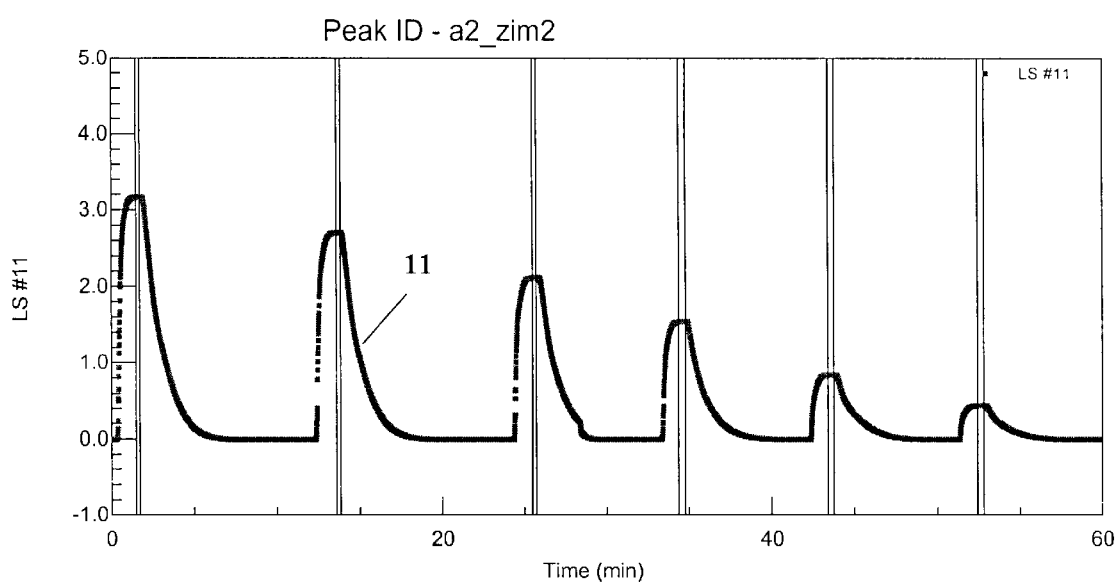
FIG. 2. The 90° light scattering signal for the series of injections used to construct the Zimm plot of 200 kED polystyrene in toluene shown in FIG. 3. This shows the plateaus achieved by each injection and the range of samples averaged together. The vertical axis is the raw detector voltage minus the solvent baseline voltage.
Figure 3:
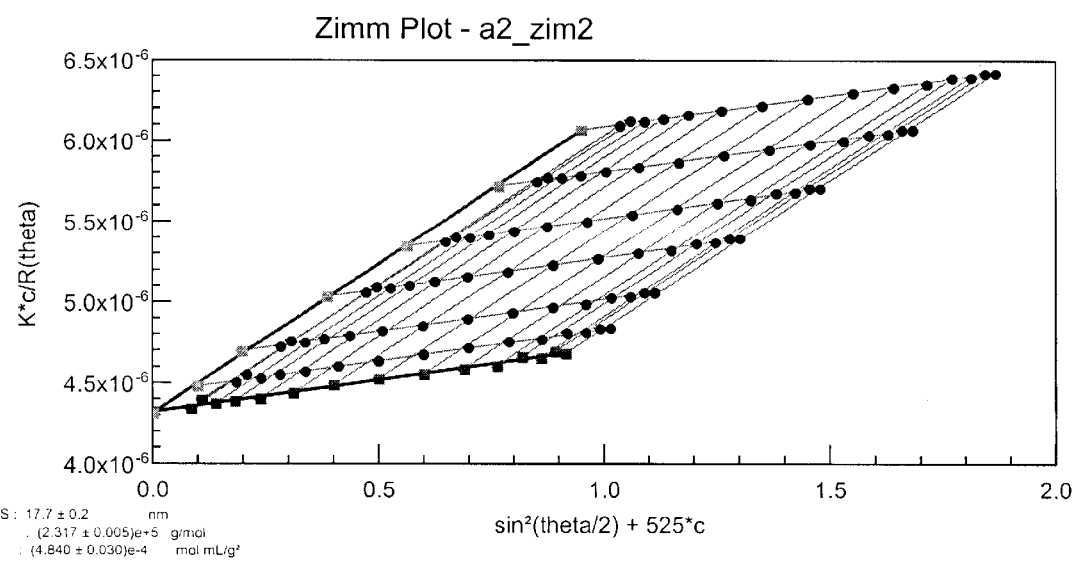
FIG. 3. Traditional Zimm plot of a narrow 200 kD polystyrene standard dissolved in toluene. The samples were created by serial dilution of a parent solution.

The sample was characterized using two methods. The first method is the traditional Zimm method. A parent sample was prepared at a concentration of 1.808 mg/ml. A series of known dilutions were prepared by diluting the parent sample. The resulting concentrations were (1.808 mg/ml, 1.4582 mg/ml, 1.0703 mg/ml, 0.7342 mg/ml, 0.3745 mg/ml, and 19 0.1879 mg/ml. These were injected using a 500 µl injection loop so that the flow cell of the MALS instrument was overfilled. A guard column was used to remove dust and to separate the dissolved gas from the sample. The raw signal 11 from 90° light scattering detector is shown in FIG. 2. The plateaus are clearly visible and a small range of data on the plateau of each peak were averaged and used to generate the Zimm plot shown in FIG. 3. The measured quantities are $M_w = 2.32 \times 10^5$ g/mol, $$\sqrt{\langle r_g^2 \rangle} = 17.7 \text{ nm},$$

and $A_2 = 4.84 \times 10^{-4}$ mol/g$^2$. The data are of high quality, but large quantities of sample are required.

Figure 4:
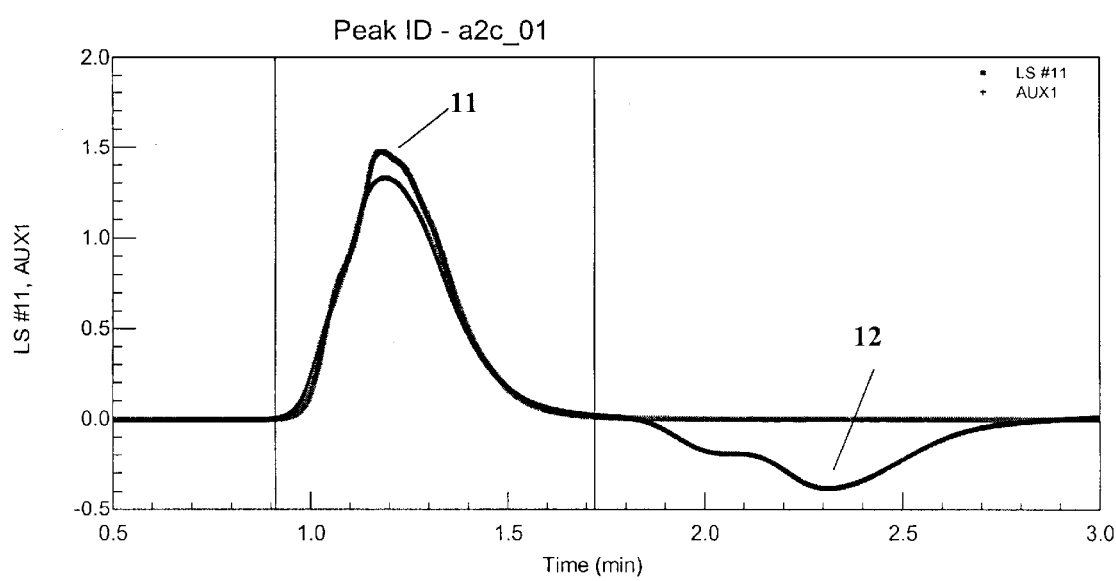
FIG. 4. A single injection used in the Trainoff-Wyatt plot shown in FIG. 5. The trace 11 is the raw 90° light scattering signal. The trace 12 is the DRI signal. It has been scaled so that its peak is 90% of the light scattering peak and it has been shifted in time to correct for the interdetector delay volume. The trailing feature in the DRI signal is due to dissolved gasses, in the sample, that are separated by the guard column. The slight difference in the peak shapes is due to interdetector band broadening. Note that it does not plateau. This is one of the six injections used to generate FIG. 5.

The second method is the subject of this invention. The same sample solutions were injected, but using a 107 µl injection loop so that the flow cell was not completely filled and plateaus were not achieved. The data from one injection is shown in FIG. 4. It shows the 90° light scattering signal 11 overlaid with the DRI signal 12. The DRI signal has been shifted in time to compensate for the delay introduced by the interdetector volume. Both have been baseline subtracted. Additionally the DRI peak has been scaled to 90% of the light scattering peak for clarity of presentation. From each injection, $\Re(\theta_k)$, $C_j$, and $v_j$ are computed without correcting for interdetector band broadening. The resulting TW plot, using the Zimm fit method, is shown in FIG. 5. The line 13 is the fit defined by Eq. (26) and the line 14 is the fit defined by Eq. (25). The results obtained were $M_w = 2.10 \times 10^5$ g/mol, $$\sqrt{\langle r_g^2 \rangle} = 18.1 \text{ nm},$$

and $A_2 = 5.13 \times 10^{-4}$ mol/ml/g$^2$.

The same data are then fit using the global fit method as shown in FIG. 6, giving the same results for the molecular parameters. Lastly the $\kappa_j$ are corrected for band broadening using the Gaussian approximation of Eq. (20). The resulting TW plot is virtually identical to FIG. 6. The derived molecular parameters are $M_w=2.10\times10^5$ g/mol, $$\sqrt{\langle r_g^2 \rangle} = 18.1 \text{ nm},$$

and $A_2=4.69\times10^{-4}$ mol/ml/g$^2$. Note that the band broadening correction has a negligible effect on $M_w$ and $$\sqrt{\langle r_g^2 \rangle},$$

but it changes $A_2$ by approximately 10%. The Gaussian approximation result is within 3% of the traditional Zimm plot method.

Lastly, let us compare the results of the Gaussian approximation to interdetector band broadening correction to those of the calibration method. In the previous analysis, the Gaussian approximation was computed independently for each peak. If we assume that the broadening is a system parameter, and is identical for each peak, one can compute the average of $D^m/D=1.099$. From the calibration method we find $D^m/D=1.060$. Therefore the two methods agree to within 4%, which is within the experimental error.

As will be evident to those skilled in the arts of light scattering, there are many obvious variations of the methods we have invented and described that do not depart from the fundamental elements that we have listed for their practice; all such variations are but obvious implementations of our invention described hereinbefore and are included by reference to our claims, which follow.

What is claimed is:

1. A method to determine the weight average molar mass $M_w$, mean square radius $\langle r_g^2 \rangle$, and $2^{nd}$ virial coefficient $A_2$ of an unfractionated sample comprising the steps of A) preparing a series of n dilutions of said sample in a suitable solvent means, said dilutions spanning a range of concentrations of about an order of magnitude;

B) providing solvent means reservoir;

C) providing pumping means by which said solvent means may be made to flow sequentially through a multiangle light scattering detection means and a concentration detection means;

D) sequentially injecting an aliquot of each said n sample dilutions;

E) collecting and storing said multiangle light scattering and concentration data in computer means at preselected flow volumetric incremental intervals, $\Delta v$, throughout each said aliquot's elution as it passes through said multiangle light scattering and concentration detector means;

F) forming the n sums corresponding to said n sample injections by said computer means, $$C_j = \sum_i c_{ij},$$

where j=1 to n, from said collected concentration data values, $c_{ij}$, over the entire concentration elution elements ij of each said sample dilution j;

G) forming the n sums corresponding to said n sample injections by said computer means, $$D_j = \sum_i c_{ij}^2,$$

where j=1 to n, from said collected concentration data values, $c_{ij}$, over the entire concentration elution elements ij of each said sample dilution j;

H) calculating the excess Rayleigh ratios $R_{ij}(\theta_k)$ from said collected light scattering data at each scattering angle $\theta_k$ for each said sample dilution j and each elution i;

I) forming the n sums $$\Re_j(\theta_k) = \sum_i R_{ij}(\theta_k),$$

j=1 to n, for each scattering angle $\theta_k$ and sample dilution j, by said computer means, over the entire light scattering elution elements i of said sample dilution j;

J) forming the ratios $D_j/C_j=\kappa_j$;

K) using said ratios $\kappa_j$ and said sums $\Re_j(\theta_k)$ for all angles k and n sample dilutions to derive said weight average molar mass, said mean square radius, and said $2^{nd}$ virial coefficient of said unfractionated sample.

2. The method of claim 1 where said weight average molar mass, said mean square radius, and said $2^{nd}$ virial coefficient of said unfractionated sample are derived by a) fitting $$\frac{K^* C_j}{R_j(\theta_k)}$$

by statistical means to the function $$\sum_{l=0}^{N_\theta} \sum_{m=0}^{N_\kappa} a_{lm} \sin^{2l}(\theta_k/2) \kappa_j^m,$$

where $N_\theta$ is the maximum degree of the angular variation fit and $N_\kappa$ is the maximum degree of the $\kappa$ variation to be fit;

b) determining therefrom the coefficients $a_{00}$ and $a_{01}$; and c) setting said weight average molar mass $M_w=1/a_{00}$, said mean square radius $\langle r_g^2 \rangle = a_{01}/2$, and said $2^{nd}$ virial coefficient $$A_2 = \frac{3\lambda_0^2 a_{10}}{16\pi^2 n_0^2 a_{00}}.$$

3. The method of claim 1 where said weight average molar mass, said mean square radius, and said $2^{nd}$ virial coefficient of said unfractionated sample are derived from a Trainoff-Wyatt plot wherein a) the data for each angle is fit as a function of $\kappa_j$ to $$\frac{K^* C_j}{R_j(\theta_k)} = \sum_{l=0}^{N_l} a_{l,k} \kappa_j^l,$$

where $a_{l,k}$ are fit parameters and $N_l$ is the order of the concentration fit;

b) the data for each injection is fit to $$\frac{K^* C_j}{R_j(\theta_k)} = \sum_{m=0}^{N_m} b_{j,m} \sin^{2m}(\theta_k/2),$$

where $b_{j,m}$ are fit parameters and $N_m$ is the order of the angle fit;

c) the fit coefficients are then fit to $$a_{0,k} = \sum_{m=0}^{N_m} u_m \sin^{2m}(\theta_k/2),$$

$$b_{j,0} = \sum_{l=0}^{N_l} v_l \kappa_j^l,$$

where $u_m$ and $v_l$ are fit coefficients; and d) said weight average molar mass is determined from $M_w = [1/u_0 + 1/v_0]$, e) said $2^{nd}$ virial coefficient $A_2 = v_1/2$, and f) said mean square radius $$\langle r_g^2 \rangle = \frac{3\lambda_0^2 M_w u_1}{16\pi^2 n_0^2}.$$

4. The method of claim 1 where the factors $D_j$ of the ratios $D_j/C_j = \kappa_j$ have been corrected for band broadening.

5. The method of claim 1 where said multiangle light scattering detector means is replaced by a single angle light scattering detector means at a selected angle a and said sums $$R_j(\theta) = \sum_i R_{ij}(\theta)$$

are formed correspondingly for a single angle.

6. The method of claim 5 where said single angle light scattering detector means is at angle $\theta = 90°$.

7. The method of claim 1 where said concentration detector means is a differential refractive index, DRI, detector.

8. The method of claim 1 where said concentration detector means is an ultra violet, UV, absorption detector.

9. The method of claim 1 where said concentration detector means is an evaporative light scattering detector.

* * * * *